United States Patent [19]

Blaine et al.

[11] Patent Number: 5,789,675
[45] Date of Patent: Aug. 4, 1998

US005789675A

[54] DISPOSABLE ELECTROMAGNETIC FLUID LEVEL SENSOR

[75] Inventors: David H. Blaine, Salt Lake City; David J. McNally, Sandy; Paul McArthur, Park City, all of Utah

[73] Assignee: Zevex, Inc., Salt Lake City, Utah

[21] Appl. No.: 511,380

[22] Filed: Aug. 4, 1995

[51] Int. Cl.⁶ .................................................. G01F 23/00
[52] U.S. Cl. ......................................... 73/290 R; 340/612
[58] Field of Search ................................. 116/109, 227; 73/290 R, 290 V; 340/621, 612, 618, 450, 450.1, 450.2, 450.3, 620, 619

[56] References Cited

U.S. PATENT DOCUMENTS

| | | | |
|---|---|---|---|
| 4,280,126 | 7/1981 | White | 340/621 |
| 4,631,529 | 12/1986 | Zeitz | 340/619 |
| 4,703,314 | 10/1987 | Spani | 340/619 |
| 4,829,448 | 5/1989 | Balding | 340/619 |
| 4,901,245 | 2/1990 | Olson | 340/621 |
| 4,908,676 | 3/1990 | Bedell | 73/61.52 |
| 4,920,336 | 4/1990 | Meijer | 340/619 |
| 4,984,462 | 1/1991 | Hass, Jr. | 340/619 |
| 5,015,995 | 5/1991 | Holroyd | 340/621 |
| 5,112,319 | 5/1992 | Lai | 116/109 |
| 5,351,036 | 9/1994 | Brown | 340/618 |
| 5,473,245 | 12/1995 | Silvus, Jr. | 73/314 |

OTHER PUBLICATIONS

McGraw–Hill Dictionary of Physics and Mathematics, McGraw–Hill, Inc., 1979, p. 626 (no month), 1979.

*Primary Examiner*—Christine K. Oda
*Attorney, Agent, or Firm*—Thorpe, North & Western, LLP

[57] ABSTRACT

A disposable fluid level sensor of the present invention determines the level of fluid in a container. A flex circuit sensor is coupled to a processing module having a power supply, the flex circuit sensor being mounted at a selectable location by an adhesive patch which holds the sensor flush against the container. The processing module hangs from the flex circuit, and provides a human perceptible indication, such as a flashing light or an audible alarm, when the fluid level drops below a desired point as determined by the sensor. The sensor detects the change in fluid level by transmitting an electromagnetic signal and determining whether there is a change in reflected energy.

24 Claims, 2 Drawing Sheets

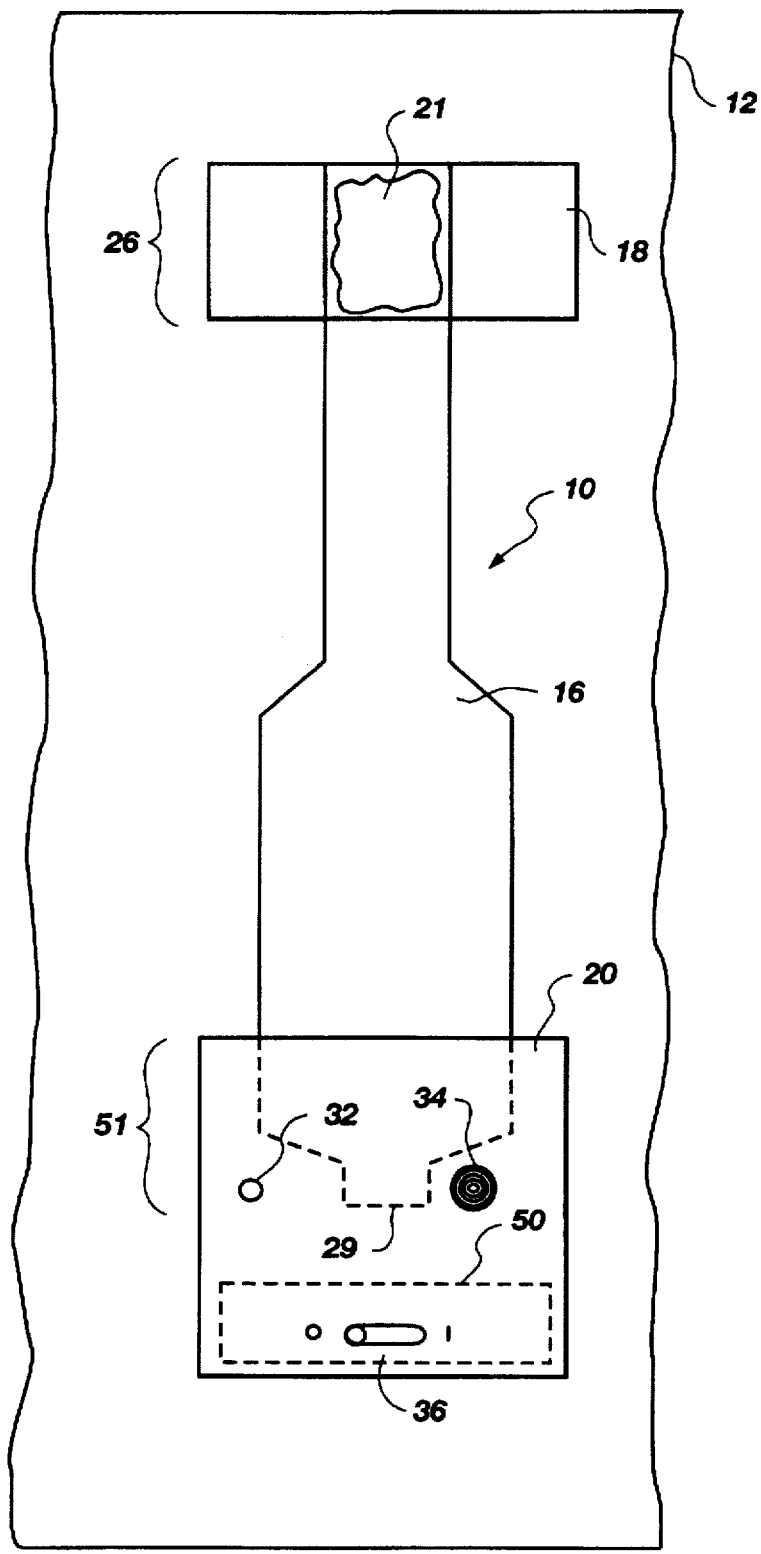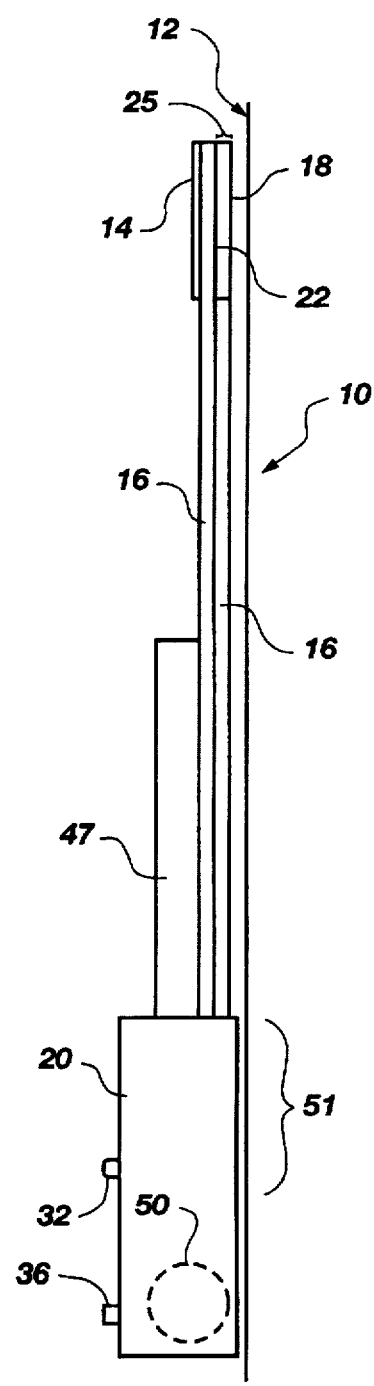
Fig. 1
Fig. 2

DISPOSABLE ELECTROMAGNETIC FLUID LEVEL SENSOR

BACKGROUND OF THE INVENTION

The present invention relates to a sensor for the noninvasive measurement of liquids within a container, and in particular, to a sensor which indicates when liquid within the container drops below a desired level.

Medical science often requires that liquids be administered to a patient in a variety of situations. These liquids include simple intravenous feeding solutions, saline solutions for providing pressure to the eye during ocular surgery, contrast media infused to enhance imaging abilities, blood administered during transfusions, and nutrient solutions delivered via an enteral feeding pump. In virtually all such situations, it could be dangerous for the liquid supply to inadvertently "run dry." In some applications, allowing the container to run dry may decrease the pressure of the liquid below that desired. In other situations, it can result in air entering the blood stream, causing complications or even death.

Several approaches have been suggested for monitoring containers of liquids so that inadvertent "running dry" can be avoided. For example, one system involves use of an electrical needle skewered into the bottom of a bottle containing liquid to be monitored. A constant electrical current is applied to the needle, and when the liquid level drops below the end of the needle, the break in the electrical current causes a lamp to light on a master control panel. A major disadvantage of this approach is that the fixed location of the needle results in a fixed triggering position. Thus, the user cannot select the liquid level at which the system will signal that the container needs to be refilled or replaced. And yet, the desired triggering position of the indicator may vary for different medical procedures. Additionally, some procedures may benefit from being able to vary the location at which the indicator signal reacts during different periods of the procedure.

An additional disadvantage of this system is that it is invasive. By placing the needle in the solution, the risk of contamination is increased.

Yet another disadvantage of such a system is that it is limited in the types of fluids which may be monitored therewith. For example, this system is designed to work with an ionic solution, but will not work will many solutions which are not ionic.

Other available systems have ultrasonic liquid level detectors for blood containers in which the transducer is placed against an exterior wall of the container. Ultrasonic signals are emitted into the container and reflected signals are used to determine when the liquid level has dropped below a designated point. The coupling between the transducer and container sidewall, however, requires that gel be placed on the sidewall to conduct the ultrasonic signals from the transducer into the container and from the container back into the transducer. This approach can be time consuming and messy as gel must be applied to the transducer or sidewall each time the two are coupled.

Other systems, such as that disclosed in U.S. Pat. No. 5,303,585, teach fluid volume sensors to determine the volume of gas or liquid within a container. However, the sensors transmit the signals to remote processing units which indicate to the user whether the volume of liquid is below the desired level.

All of these systems lack provision of a simple, noninvasive, inexpensive and disposable sensor which may be easily installed on the monitored container without cumbersome cables or coupling gel. Thus, there is a need for a simple, inexpensive and disposable sensor which may be quickly and conveniently applied to a container to be monitored.

A feature common to all of the sensor systems mentioned above is that the sensors are designed for placement on jars, bottles and containers which have rigid sidewalls. This limitation is due to the type of sensor being used. Specifically, the sensors are designed to detect signal reflections from the container sidewalls. The sensors also require reliable contact when mounted flush to the container to assure transfer of the majority of signal energy between the sensor and the container at all times. Therefore, there is also a need for a system which will enable monitoring of the fluid level within the numerous types of containers which do not have rigid sidewalls, such as plastic bags. Such bags constantly change shape as fluids within the bags are drained, and which do not offer sidewalls that guarantee focused reflection of a signal in any particular direction.

SUMMARY OF THE INVENTION

It is an object of the invention to provide a noninvasive liquid level indicator especially suitable for medical and other applications requiring care in the administration of liquids.

It is another object of the invention to provide a noninvasive liquid level indicator which may be easily installed on and removed from containers containing the liquid to be monitored.

It is a further object of the invention to provide such a noninvasive liquid level indicator which, when installed on containers, does not require the use of ultrasonic gel or couplant.

It is an additional object of the invention to provide such a noninvasive liquid level indicator which may be manually positioned for measuring different and selectable "triggering" levels in a container.

It is still a further object of the invention to provide such a noninvasive liquid level indicator which may be coupled to containers without rigid sidewalls, and yet still provide an accurate indication of the level of the liquid within.

Still yet a further object of the invention is to provide a noninvasive liquid level indicator which has a disposable sensor portion and a reusable processing portion so as to economically determine a level of the liquid in a container.

These and other objects of the invention are realized in a liquid level indicator for determining the level of liquid in a container, which includes a sensor mechanism powered by an electric current, a means for mounting the sensor, a processing module, and a means for transmitting signals between the processing module and the sensor. The sensor is mountable by adhesive integral to the sensor at selectable locations on the exterior of the container. Responsive to the current, the sensor mechanism generates a level detection signal which is applied to the container at the level at which the sensor mechanism is positioned and which indicates whether or not fluid in the container is above or below the level of the sensor. In particular, the processing module generates a human perceptible signal indicating whether the fluid is present at the same level as the sensor mechanism.

The exact positioning of the sensor mechanism on the container depends on the application for which the fluid in the container is used, as well as the personal preference of medical personnel.

In accordance with the invention, the sensor mechanism includes an electromagnetic sensor made of a flex circuit which securely couples to an exterior surface of a container. The electromagnetic sensor transmits an electromagnetic signal, typically in the 1 MHz to 10 GHz range, into the container and receives reflected signals. The electromagnetic sensor is coupled to a monitoring mechanism which measures the amount of reflected energy, which is indicative of the reflection coefficient of the container, or the container and liquid if the liquid is above the sensor. A small amount of reflected energy signifies that the transmitted energy has coupled to the liquid and consequently has been dispersed in the liquid. In contrast, a large amount of reflected energy signifies that there was no liquid at the level of the sensor for the transmitted signal to be coupled to, resulting in almost all energy being reflected back to the sensor. Therefore, when the amount of reflected electromagnetic energy sharply increases due to a change in the liquid level in the container, the monitor emits an indicator signal, warning the user that the liquid has dropped below the designated point.

BRIEF DESCRIPTION OF THE DRAWINGS

The above and other objects, features and advantages of the invention will become apparent from a consideration of the following detailed description presented in connection with the accompanying drawings, in which:

FIG. 1 shows a plan view of the disposable fluid level sensor with an accompanying processing module, made in accordance with the present invention;

FIG. 2 shows a side view of the disposable fluid level sensor with the accompanying processing module of FIG. 1;

DETAILED DESCRIPTION

Figures 3, 4:
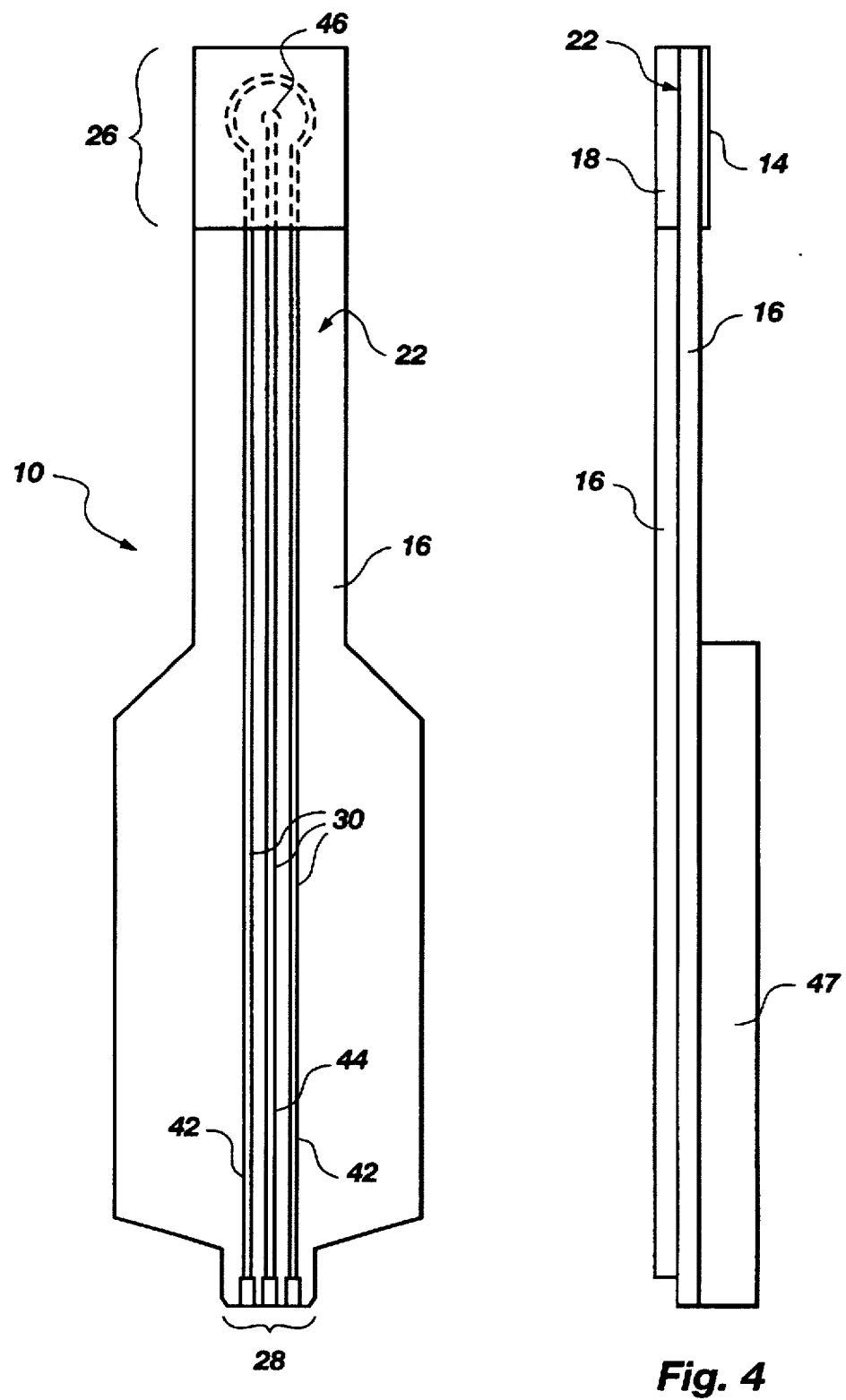
FIG. 3 shows a plan view of the flex circuit electromagnetic sensor of the present invention.
FIG. 4 shows a side view of the flex circuit shown in FIG. 3.

Reference will now be made to the drawings in which the various elements of the present invention will be given numeral designations and in which the invention will be discussed so as to enable one skilled in the art to make and use the invention.

However, before going into detail, it is advantageous to first describe what the present invention accomplishes. Components of the present invention combine to provide an electromagnetic signal from an antenna coupled to a container. Electromagnetic energy is either dispersed by coupling with a liquid within the container if the liquid is at or above the level where the antenna is attached, or the energy is not dispersed because the liquid is below the antenna. By measuring reflected electromagnetic energy, it is then possible to determine if liquid is above or below the antenna location. A large amount of reflected energy means that there is no liquid at the position of the antenna with which to couple, whereas a small or negligible amount of reflected energy means that liquid is present.

FIG. 1 shows a noninvasive liquid level indicator 10 made in accordance with the present invention as it would be mounted to an exterior sidewall (plane of paper) of a container 12. The indicator 10 includes a flex circuit sensor 16, an integral adhesive patch 18, and a processing module 20.

The flex circuit sensor 16 couples to the integral adhesive patch 18 at a transmitting and receiving end 26. The adhesive patch 18 has an attachment surface 21 to which is applied an adhesive material. The adhesive material securely binds the attachment surface 21 to a front side of the flex circuit transmitting and receiving end 26 so as to provide a means of adhering/securing the sensor 16 to the container 12. The attachment surface 21 is sufficiently large so as to securely couple the flex circuit sensor 16 to a container 12.

The flex circuit sensor 16 also couples to the processing module 20 by a flex circuit edge connector 28 (FIG. 3) that slides into a friction coupling connector 29.

The processing module 20 includes a visual indicator means 32, such as a small light, and an audible indicator means 34, such as a speaker, to warn the user when the fluid in a container passes below the position of the transmitting and receiving end 26 of the flex circuit sensor 16. The processing module 20 also includes an on/off switch 36 to conserve power source 50 when the sensor 10 is not in use.

FIG. 2 is a profile view of the liquid level indicator 10 shown in FIG. 1. Distinct layers with exaggerated thicknesses of the flex circuit 16 are shown to clearly distinguish the various components of the invention. For example, while a gap 25 appears to indicate a substantial separation between the flex circuit transmitting and receiving end 26 and the container 12, it is only the scale of the drawing. The actual gap 25 is approximately 0.005 inches, which accommodates the adhesive patch 18. The nature of the flex circuit sensor 16 enables it to bend so as to be mounted flush against the container 12 with the adhesive patch 18.

A conductive patch 14 is placed on the flex circuit sensor 16 at the transmitting and receiving end 26. The conductive patch 14 is on the side of the flex circuit sensor 16 opposite the adhesive patch 18 and covers the entire transmitting and receiving end 26. Alternatively, the conductive patch 14 is fabricated as part of the flex circuit.

The purpose of the conductive patch 14 is to electrically shield the transmitting and receiving end 26 in such a manner as to force the entire transmitted electromagnetic signal into the container 12. This prevents the flex circuit sensor 16 from detecting air on the backside of the transmitting and receiving end 26, and reduces interference from other electromagnetic energy sources.

Combined with the substrate of the flex circuit 16 is a nonconductive material 47 attached to a portion 51 of the flex circuit sensor 16 which slides into the processing module 20. The nonconductive material 47 is a support which stiffens the flex circuit sensor to give the flex circuit sensor 16 strength so as to not unduly bend and prevent a reliable contact when inserted in the processing module connector 29. As shown in FIGS. 1 and 2, the processing module 20 is suspended from the container 12 by the adhesive patch 18 and the flex circuit sensor.

When the liquid level indicator 10 is not in use, the on/off switch 36 can be moved into an off position to conserve power in the power source 50. Because the processing module 20 is not disposable, the power source 50 is stored within the processing module 20 so that the power source 50 is user replaceable. In a typical embodiment, the power source 50 would contain enough charge to enable the liquid level indicator 10 to function for about 50 hours in an "on" mode. It is envisioned that further refinement will show that the optimum power source 50 will likely be a lithium battery.

This figure also shows that the on/off switch 36 and the visual indicator means 32 extend slightly above an outward surface of the processing module 20. This feature makes the liquid level indicator 10 easier to turn on and off, and allows the visual indicator means 32 to be seen from a wider angle of view.

Referring now to the structure of FIGS. 3 and 4, there is shown a more detailed view of the flex circuit sensor 16 so as to illustrate the specific components of the flex circuit sensor. The flex circuit sensor 16 is oriented in FIG. 3 such that the surface 22 which faces a container sidewall is shown, without the processing module 20 attached to the flex circuit edge connector 28. Specifically, this view provides detail of the flex circuit traces 30, edge connector 28.

The flex circuit sensor 16 is designed to transmit and receive a signal from a transmitting and receiving end 26. An edge connector 28 is formed at the opposite end of the flex circuit 16 for coupling to the processing module 20 as previously described. The distance between flex circuit ends 26 and 28 is approximately 6 centimeters in a preferred embodiment, but could be longer or shorter. Copper traces 30 electrically couple the transmitting and receiving end 26 to the edge connector 28.

In a preferred embodiment, the circuit traces 30 are formed of copper with a thin layer of gold deposited thereon to prevent tarnishing of the copper surface. This gold layer also helps to ensure that the edge connector 28 makes a reliable electrical contact with the processing module friction connector 29.

As shown, the three copper traces 30 actually form only two distinct paths. The two outer traces 42 beginning at the edge connector 28 run parallel to the center trace 44, and form a circle around the center trace 44 at the transmitting and receiving end 26 of the flex circuit sensor 16. The center trace 44 has formed on an end 46 thereof a small copper disk 46.

Having described components of the present invention in detail, it is now possible to see how they provide the necessary structure and circuits to accomplish the objects of the invention. For example, the flex circuit sensor 16 acts as an "antenna" which operates on the principle of coupling electromagnetic energy to different media and then measuring reflected energy. A full container 12 or one in which a fluid is above or at a position where the transmitting and receiving end 26 is currently attached reflects almost no electromagnetic energy to the flex circuit sensor 16 of the present invention because electromagnetic energy broadcast by the flex circuit sensor 16 couples to the fluid within the container 12 and is dispersed.

On the other hand, if the container 12 is empty or there is no fluid in the container 12 at the position of the transmitting and receiving end 26, almost all of the electromagnetic energy is reflected back to the flex circuit sensor 16 because there is no fluid to couple with the energy and cause its dispersal. Unlike an acoustic sensor where the timing between emission of a broadcast signal into a container and receipt of a return signal to the antenna is the critical parameter which indicates the presence of fluid, it is simply the presence or absence of reflected electromagnetic energy which is indicative of fluid in a container 12. Thus, if the fluid has passed below the position of the sensor transmitting and receiving end 26, there is a reflection of a substantial portion of incident electromagnetic energy, and the liquid level indicator 10 alerts a user that the fluid in the container 12 has fallen below the level of the transmitting and receiving end 26 of the flex circuit sensor 16.

To obtain a reliable result from the liquid level indicator 10, the flex circuit sensor 16 must be securely attached to the sidewall of the container 12 by the adhesive patch 18 so as to ensure maximum transfer of electromagnetic energy emitted from the flex circuit sensor 16 to the coupled media, in this case the container 12 and possibly the fluid therein.

Maximum electromagnetic energy transfer is crucial because the liquid level indicator 10 determines the level of liquid as a function of the amount of total electromagnetic energy transmitted versus total electromagnetic energy reflected back to the flex circuit sensor 16. A flex circuit sensor 16 held loosely against the container 12 is likely to result in a false indication that a liquid has fallen below the level of the transmitting and receiving end 26 of the flex circuit sensor 16.

While the type of adhesive material used to secure the liquid level indicator 10 to the container 12 is not a material element of the present invention, the use of adhesive results in the need to create a partially self-destructing flex circuit sensor 16. The adhesive patch 18 is sufficiently strong so as to be able to secure the flex circuit sensor 16 flush against the container 12 to ensure maximum electromagnetic energy transfer. However, such a strong adhesive is required to ensure maximum energy transfer that it is unlikely that the adhesive patch 18 could be reliably reattached to a container 12 once it is removed. If the flex circuit sensor 16 position must be changed on the container 12, a new disposable flex circuit sensor 16 must be applied at a new position, and the processing module 20 removed from the used flex circuit sensor 16 and coupled to a new flex circuit sensor.

To ensure that the flex circuit sensor 16 is not reused, it is designed to be unusable once the flex circuit 16 is pulled in sufficient tension to remove the adhesive. It is currently envisioned that a preferred embodiment is configured so that removing the flex circuit 16 will cause delamination of flex circuit copper traces 30, while leaving the adhesive patch 18 attached to the container 12. Such damage will force an operator to place a new flex circuit sensor 16 at a new location on the same container 12 because the flex circuit sensor 16 will be damaged and because the adhesive can no longer provide a reliable attachment to the container 12. Alternatively, the processing module 20 could produce an alarm signal indicative of the decoupling of the transmitting and receiving end 26 of the flex circuit sensor 16 from a container.

The processing module 20 contains the circuitry necessary to generate an electromagnetic signal to be transmitted from the flex circuit transmitting and receiving end 26, as well as to measure the amount of reflected energy after transmission by methods well known to those skilled in the art. When reflected energy increases sharply, the circuit activates the LED 32 and the speaker 34, alerting someone that the liquid level is below a predetermined level defined by the position of the transmitting and receiving end 26 of the flex circuit sensor 16 on the container 12.

The processing module 20 is also constructed of sufficiently small and lightweight materials so as to be light enough to hang suspended from the edge connector 28 without danger of decoupling. Such a material is impact resistant plastic. While the edge connector 28 is presently in tight sliding engagement with the friction coupling connector 29 of the processing module 20, any other connector which will enable the processing module 20 to hang from the flex circuit sensor 16 without pulling free by its own weight may be used.

The flex circuit sensor 16 can be manufactured of any appropriate materials which enable the circuit to function as described above. In the preferred embodiment, the flex circuit 16 is constructed of a substrate composed of Kapton or some other suitable plastic-like polyamide material. The formation of the traces 30 can be accomplished by numerous methods which will be apparent to those skilled in the art of forming flex circuits.

Further discussion of the copper traces 30 is also useful to provide greater understanding of how the flex circuit sensor 16 operates. The function of the outer traces 42 is twofold. First, the traces 42 act as ground plane shielding on either side of an emissive line (center trace 44), thereby reducing stray electromagnetic emissions. Second, the traces 42 act to reduce the susceptibility of the center trace 44 to interference from other electromagnetic emissions which might interfere with the antenna operation. It is envisioned that the traces 30 will have an impedance of approximately 50 ohms.

To further clarify use of the electromagnetic sensor, the flex circuit transmitting and receiving end 26 is firmly held against a sidewall 12 of the container by the adhesive patch 18. The processing module 20, powered by a power source such as a battery 50, sends an electromagnetic signal to the transmitting and receiving end 26 through the center trace 44. The flex circuit sensor 16 typically transmits an electromagnetic pulse in the range of 1 MHz to 10 GHz. It is believed, however, that refinement of the range to occur during further testing will result in an actual broadcast frequency of approximately 500 Mhz. Preferably, the antenna is a driven by a gated pulse signal of about 5 to 10 volts peak to peak in amplitude.

If the flex circuit sensor 16 has been properly applied to the container 12 and there is fluid within the container 12 above where the transmitting and receiving end 26 of the flex circuit sensor 16 is attached, a negligible amount of electromagnetic energy is reflected back to the flex circuit sensor 16. In response, any reflected electromagnetic energy is sent through the traces 42 and 44 to the processing module 20, where the signal is processed to determine the quantity of reflected energy. The processing module 20 actuates a visual indicator 32 and/or some other perceptible indicator, such as an audible indicator 34, to inform the user that the fluid level is adequate. Alternatively, the processing module 20 could be programmed or wired to not emit any indication signals until the liquid level passes below the transmitting and receiving end 26 of the flex circuit sensor 16.

The processing module 20 monitors the liquid level in a container 12 at least approximately 10 times per second. Consecutive responses are averaged to reduce the bit error rate and eliminate the influence of noise on the system. Upon receiving several consecutive negative responses, defined as a sharp increase in reflected electromagnetic energy, the processing module 20 activates the alarm mechanisms.

The processing module 20 provides specific signals indicating the mode and status of operation. For example, the processing module 20 issues a single LED 32 pulse every five seconds to indicate a safe (high) liquid level indication. The module 20 issues an audible alarm through the speaker 34 consisting of four pulses in one second, repeated every five seconds, if there is an unsafe (low) liquid level indication. The LED 32 also blinks continuously at a rate of four times per second at a low liquid level condition. The module 20 also issues an audible alarm from the speaker 34 if the flex circuit sensor 16 is not within the vicinity of a detection media, or if the flex circuit sensor 16 is not properly connected to the processing module 20 when power is switched on.

When 50 hours of battery life have been expended, the liquid level indicator 10 provides an early warning audio alert to indicate a low battery condition. In a preferred embodiment, the audio warning alert consists of a single pulse repeated every 10 seconds. During this period of low battery alert, the sensor 10 continues to operate, including the single LED pulse repeated every 5 seconds. After approximately 30 minutes of low battery alert, an audio alarm sounds continuously at a rate of 4 pulses per second until the battery is completely expended. During this low battery alarm period, the LED 32 is completely off.

The motivation for creating this liquid level indicator 10 which uses electromagnetic signals is a desire to simplify operation of a liquid level sensor, and to create a more versatile sensor which may be used with both rigid and nonrigid containers while maintaining the same level of accuracy. It is believed that an electromagnetic liquid level indicator 10 accomplishes this simplification and versatility because for electromagnetic waves in the sub-gigahertz range, container wall thickness is much smaller than one wavelength. This means reflections off the outer wall surface of the container are approximately 180° out of phase with those off the inner wall surface. The net effect is that the container is virtually invisible, and the reflected pulse magnitude depends only on the impedance match of the antenna to the contents of the container. This is not true with ultrasound because the sonic wavelength is close to container thickness in many cases, and because acoustic impedances are such as to produce phase differences generally not close to 180°. This means reflections off the container dominate the processed signal, (i.e. the container is acoustically present). Ultrasonic sensing is, therefore, highly sensitive to container wall thickness, impedance and acoustic velocity.

Another advantage of this electromagnetic liquid level indicator 10 is that placement of the flex circuit sensor 16 is much simpler. No mounting projections are required to ensure that the flex circuit sensor 16 is oriented properly with respect to a container 12 and a reflected signal. It is only important that the flex circuit sensor traces 30 on the transmitting and receiving end 26 be flush against a container sidewall 12 so that transmitted electromagnetic energy is coupled to the attached container 12 resulting in electromagnetic energy either being dispersed or reflected.

In addition to rigid wall containers such as glass balanced saline solution containers, this method for determining the level of liquid is also useful for thin walled plastic containers such as the containers used for blood, saline, medication and enteral feeding solutions. Unlike a glass container, the walls of a plastic container may collapse towards each other in an uncontrolled, random manner with a decrease in fluid volume within the container. Thus, the fact that the container can be flexible, or that a sidewall opposite to the attached container sidewall is not parallel to the coupled sidewall is no longer relevant to sensor accuracy or reliability with the present invention.

By applying the embodiment of the present invention and obvious modifications thereto, medical personnel can ensure that balanced saline solution and numerous other containers do not accidentally "run dry". The embodiment of the present invention can be used to detect air bubbles passing through medical tubing or non-metallic industrial hoses or piping, as it detects the presence and absence of liquid contained within the tubing. The embodiment can also be applied to numerous liquid level monitoring applications outside the medical environment, where accurate, low-cost liquid level monitoring on non-metallic tanks or vessels is desired.

It is to be understood that the above-described embodiments are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A fluid level sensor for use in detecting the existence of fluid at a predetermined location in a container having sidewalls, said sensor comprising:

an electromagnetic sensor means disposable at a predetermined location on a sidewall of the container for developing a electromagnetic level detection signal for transmission into the container and for receiving reflected electromagnetic signals therefrom, the electromagnetic sensor means comprising an antenna;

power supply means for supplying electrical current to said electromagnetic sensor means;

attaching means coupled to the sensor means for holding the sensor means at the predetermined location along the sidewall of the container such that the antenna is attachable to the sidewall of the container at the predetermined location;

a processing means coupled to the electromagnetic sensor means for processing electromagnetic signals received by the electromagnetic sensor means so as to determine whether fluid is present at the predetermined location, and for selectively developing a signal responsive to the signals received from the electromagnetic sensor means; and indication means for developing a human perceptible signal responsive to signals received from the processing means.

2. A fluid level sensor as in claim 1, wherein the electromagnetic sensor means has front and back sides and wherein the attaching means comprises an adhesive patch having an adhesive side, said adhesive patch being coupled by the adhesive side to the container and integral to the front side of the electromagnetic sensor means so as to hold the front side of the sensor means against the container.

3. A fluid level sensor as in claim 1, wherein the power supply means comprises a battery.

4. A fluid level sensor as in claim 1, wherein said indication means includes means for producing an audible signal when the fluid in the container falls below the location of the sensor means on the sidewall thereof.

5. A fluid level sensor as in claim 1, wherein said indication means includes means for producing a visual signal when the fluid in the container falls below the location of the sensor means on the sidewall thereof.

6. The fluid level sensor as in claim 1, wherein the electromagnetic sensor means is temporarily coupled to the processing means such that the electromagnetic sensor means is disposable, and the processing means is reusable.

7. A fluid level sensor as in claim 1, wherein said indication means includes means for producing a second human perceptible signal as long as the sensor means is developing the level detection signal.

8. A fluid level sensor as in claim 7, wherein the indication means producing the second human perceptible signal comprises an intermittent light.

9. The fluid level sensor of claim 1, wherein the sensor further comprises means for suspending the processing means from the container.

10. A fluid level sensor for use in detecting a level of fluid in a container having sidewalls, said sensor comprising:

an electromagnetic sensor means disposable at a predetermined location on a sidewall of the container for developing a level detection signal, the sensor means comprising means for developing an electromagnetic signal which, when applied to the container, transmits an electromagnetic signal used in determining whether fluid is at the location of the sensor means on the sidewall thereof said means for developing an electromagnetic signal comprising a flex circuit disposed so as to be held flush against the container sidewall by the attaching means;

power supply means for supplying electrical current to said electromagnetic sensor means;

attaching means coupled to the sensor means for holding the sensor means at a predetermined location on the sidewall of the container;

a processing means coupled to the electromagnetic sensor means for processing signals received by the electromagnetic sensor means so as to determine whether fluid is present at the predetermined location, and for selectively developing a signal responsive to the signals received from the electromagnetic sensor means; and indication means for developing a human perceptible signal responsive to signals received from the processing means.

11. The fluid level sensor as in claim 10, wherein the flex circuit has formed thereon a pair of circuit traces, an outer circuit trace surrounding a length of an inner circuit trace in a plane of the flex circuit, at least one of the traces acting as an antenna to transmit and receive electromagnetic energy therefrom, and at least one trace acting as a ground shield to reduce stray emissions and reduce the susceptibility of the inner circuit trace to electromagnetic interference.

12. The fluid level sensor as in claim 11, wherein the sensor means is uncoupled from the container which activates an alarm means to indicate that the sensor means is uncoupled.

13. The fluid level sensor as in claim 11, wherein the sensor means is uncoupled from the container and thereby rendered inoperative by destruction of the sensor means.

14. The fluid level sensor as in claim 13, wherein the sensor means is rendered inoperative by delamination of the flex circuit outer circuit trace and inner circuit trace.

15. The fluid level sensor as in claim 10, wherein the flex circuit transmits and receives electromagnetic energy in the range of 1 MHz to 10 GHz.

16. The fluid level sensor as in claim 15, wherein the flex circuit transmits and receives electromagnetic energy at approximately 500 MHz.

17. The fluid level sensor as in claim 10, wherein the processing means is coupled to the flex circuit at a flex circuit coupling end, the processing means being suspended below the flex circuit and thereby positioned adjacent to the container by the attaching means.

18. A fluid level sensor for use in detecting the level of fluid in a container having a sidewall, said sensor comprising:

a disposable electromagnetic sensor means including a sensor and a circuit powered by electrical current for developing an electromagnetic level detection signal which when applied to the container from a location of the sensor means on a sidewall thereof will provide a human perceptible indication of whether fluid in the container is at the level of said location responsive to reflected electromagnetic signals, the disposable electromagnetic sensor means comprising an antenna attachable to the container;

a battery connected to the sensor means for supplying electrical current to said sensor means;

a reusable processing means in which the battery and at least a portion of the sensor means are disposed within, the reusable processing means being selectively attachable and detachable from the antenna of the electromagnetic sensor means; and attaching means joined to the antenna of the electromagnetic sensor means for holding the sensor means at a predetermined location on the sidewall of the container.

19. The fluid level sensor of claim 18, wherein the processing means generates an indicator signal in response to changes in the electromagnetic level detection signal, and wherein the sensor means further comprises a visual indicator and an auditory indicator responsive to said indicator signal for generating a human perceptible signal when the level of fluid within the container passes below the location of the sensor means on the sidewall thereof.

20. A method for monitoring the presence of liquid at a predetermined level within a container, the method comprising:

a) providing an electromagnetic signal emitting and sensing means, the electromagnetic signal emitting and sensing means comprising a flexible antenna;

b) positioning said electromagnetic signal emitting and sensing means at a predetermined level outside of the container so as to attach the flexible antenna to the container and emit electromagnetic signals into the container and receive electromagnetic signals from the container, so that the presence of liquid at the predetermined level point will cause the electromagnetic signal sensing means to receive a different amount of reflected electromagnetic energy than will absence of the liquid at the predetermined level; and c) generating a human perceptible signal in response to a change in the amount of reflected electromagnetic energy received by the electromagnetic signal sensing means.

21. The method for monitoring the presence of liquid as defined in claim 20, wherein the human perceptible signal is generated in response to change from a state of negligible reflected electromagnetic energy to a state of substantial reflected electromagnetic energy.

22. The fluid level sensor of claim 20, wherein step (b) comprises, more specifically, attaching a flexible antenna to the container.

23. The fluid level sensor of claim 20, wherein step (c) further comprises attaching a processing means to the flexible antenna so that the processing means is suspended from the antenna, and generating a human perceptible signal with the processing means in response to a change in the amount of reflected electromagnetic energy received by the electromagnetic signal sensing means.

24. A fluid level sensor for use in detecting the level of fluid in a container having a sidewall, said sensor comprising:

a disposable eletromagnetic sensor means including a sensor and a circuit powered by electrical current for developing an electromagnetic level detection signal between 1 MHz to 10 GHz which when applied to the container from a location of the sensor means on a sidewall thereof will provide a human perceptible indication of whether fluid in the container is at the level of said location, said electromagnetic sensor means comprising a flex circuit;

a battery connected to the sensor means for supplying electrical current to said sensor means;

a reusable processing means in which the battery and at least a portion of the sensor means are disposed within; and attaching means joined to the sensor means for holding the flex circuit at a predetermined location and flush against the sidewall of the container.

* * * * *